United States Patent [19]

Huber

[11] 4,165,219

[45] Aug. 21, 1979

[54] ANALYSIS OF SOLUTIONS USING CHROMATOGRAPHIC COLUMN

[75] Inventor: Walter Huber, Ludwigshafen, Fed. Rep. of Germany

[73] Assignee: BASF Aktiengesellschaft, Fed. Rep. of Germany

[21] Appl. No.: 763,137

[22] Filed: Jan. 27, 1977

[30] Foreign Application Priority Data

Feb. 7, 1976 [DE] Fed. Rep. of Germany ....... 2604832

[51] Int. Cl.² ............................................ G01N 31/08
[52] U.S. Cl. ............................ 23/230 R; 73/61.1 C; 210/31 C; 422/70
[58] Field of Search .......................... 23/230 R, 232 C; 73/23.1, 61.1 C; 210/31 C

[56] References Cited

U.S. PATENT DOCUMENTS

| | | | |
|---|---|---|---|
| 2,797,149 | 6/1957 | Skeggs | 23/230 R |
| 3,230,048 | 1/1966 | Skeggs | 23/230 R X |
| 3,794,467 | 2/1974 | Adams et al. | 23/230 R |
| 3,996,003 | 12/1976 | Fine et al. | 23/232 C X |
| 4,009,998 | 3/1977 | Benningfield, Jr. | 23/230 R |
| 4,013,413 | 3/1977 | Stewart et al. | 23/230 R |

OTHER PUBLICATIONS

Hishta et al., Anal. Chem. 32, 1730 (1960).
Begoza et al., Anal. Chem. 38, 1042 (1966).
McEwen, D. J., Anal. Chem. 38, 1047 (1966).
Cram et al., Anal. Chem. 48, 411 R, 426 R (1976).

*Primary Examiner*—R. E. Serwin
*Attorney, Agent, or Firm*—Keil & Witherspoon

[57] ABSTRACT

A process for the analysis of aqueous solutions, in which the sample is introduced into a stream of liquid color reagent and the reaction product formed in a chromatogaphic column under pressure is measured in a suitable detector.

4 Claims, 3 Drawing Figures

ANALYSIS OF SOLUTIONS USING CHROMATOGRAPHIC COLUMN

The present invention relates to a process for the analysis of aqueous or non-aqueous solutions, in which the sample is introduced into a stream of reagent and the reaction product formed is measured in a suitable detector.

U.S. Pat. No. 2,797,149 discloses that analyses of solutions can be carried out by combining streams of reagents and streams of samples with one another, passing them through delay spirals and then carrying out measurements on the streams by means of a photometer. In order to avoid entrainment effects in the relatively thick lines and in order to improve mixing, air bubbles are forced into the stream at short intervals. This makes the construction of the apparatus relatively complicated, so that this process has only found acceptance where a very large number of analyses of the same type has to be carried out continuously.

Further, Danish Patent Application No. 4,846/74 discloses that very rapid analyses can be carried out continuously by injecting a relatively large amount of sample into a stream of reagent which is conveyed at very high speed through a capillary tube. In this case, virtually no entrainment occurs and mixing is effected by the high flow velocity. A disadvantage of this method is that fairly long residence times, which are sometimes unavoidable due to the low rate of the chemical reaction, can only be achieved with difficulty.

It is an object of the present invention to provide a process according to which the parameters which determine whether optimum reaction with the reagent occurs, namely 1. mixing in a very closely defined ratio,
2. residence time and
3. temperature can be freely selected, substantially independently of one another.

We have found that this object is achieved, according to the invention, by carrying out the reaction in a chromatographic column which is filled with an inert, finely divided material, eg. glass beads of from 50 to 200 μm diameter. A combination, designed for the specific object involved, of capillary tubes and of columns known from liquid-phase chromatography, is used to transport the stream of reagent. The mixing of the sample with the stream of reagent is very dependent on the thickness of the layer of the transported solution. After injection, such mixing is initially both desirable and necessary to enable the reaction to take place at all. Preferably, the mixing is effected in a capillary tube, the diameter of which is not excessively low. A particularly high flow rate is not necessary. More vigorous mixing is disadvantageous since it reduces the sensitivity of the process. Hence, the thickness of the layer of solution must be kept low after the initial mixing. The use of thin capillary tubes for this purpose would, however, result in extremely short residence times, because of the low dead volume. Chromatographic columns with a variety of diameters which can be selected as desired are far more suitable for this purpose, since the dense packing of a finely divided, inert material greatly restricts diffusion in the lengthwise direction. Preferably, glass beads of very small diameter are used as such a packing material. By suitably selecting the diameter and length of the columns, it is possible to regulate the dead volume and hence the residence time of the solution in the column within wide limits without an unacceptable increase in the lengthwise diffusion of the sample and hence in the degree of mixing. At the same time, the column can be heated in order to accelerate the reaction.

The second effect achieved by the invention is also very important in practice. As a result of heating the reaction solution, gas bubbles can very easily be evolved if the process is carried out under atmospheric pressure, and these bubbles greatly interfere with the photometric determination. However, when using a chromatographic column an increase in pressure occurs, which depends on the length and diameter of the column, the fineness of the support material and the magnitude of the transport rate, and this increase prevents the evolution of gas bubbles. A particularly effective measure is to provide, downstream from the photometric measuring cell, a second column which serves purely as a braking column and, as a result of its dynamic resistance, also increases the pressure in the measuring cell. In this way, it is also possible to analyze solutions which, like, say, acidified carbonate solutions, tend to evolve gas.

Another embodiment of the invention makes it possible to set the sample/reagent dilution ratio precisely. It is true that in the experimental arrangement already described, this ratio can be varied, but fundamentally it is not defined. A defined dilution ratio can be achieved by combining a stream of reagent and a stream of solvent (i.e. of the solvent of the sample to be analyzed) in a defined ratio by means of two pumps and feeding the combined stream to the detector cell. In this case, the sample is injected into the stream of solvent. Provided a sample loop of sufficient volume is used and accordingly diffusion effects in the edge zones can be neglected, the desired defined dilution ratio is achieved in the central portion of the amount injected.

An advantage of this process is the maximum sensitivity of the determination, but its disadvantages are the increased cost and the longer time required for the analysis.

Further possible ways of setting up the system arise when the apparatus is used for monitoring production. Instead of batchwise operation, the sample can be mixed continuously, by means of a pump, with the reagent which is also delivered by a pump. If the sample has an intrinsic color which is responsible for a greater or lesser blank reading, which may even fluctuate, the following procedure can be adopted: the sample stream is mixed with a stream of reagent, but the latter only contains the substances required to form the optimum reaction medium (eg. a buffer solution). Thereafter, the actual color reagent is injected. This produces a peak on a base line which corresponds to the blank reading of the sample solution. In this way, the blank reading can be identified and eliminated. To use this method, the amount injected must be kept low.

The invention can best be understood by reference to the attached drawing in which.

Figure 1:
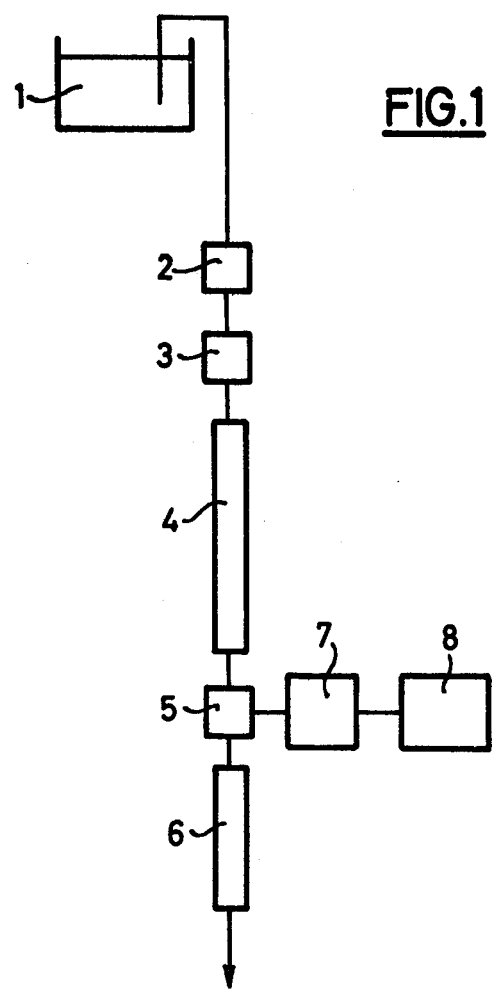
FIG. 1 is a schematic representation of a measuring device for determining the concentration of a substance in a solution.

In FIG. 1, the color reagent is drawn from a stock vessel 1 by means of a pump 2 and is transported by means of a metering device 3 into a column 4 having a detector cell 5. The metering device 3 can be an injection molding fitted with a rubber membrane or, preferably, a sample loop of low volume. 6 is a braking column intended to keep the detector cell 5 under pressure. The signal generated by the detector cell 5 is fed by an amplifier 7 to a recorder 8.

Figure 2:
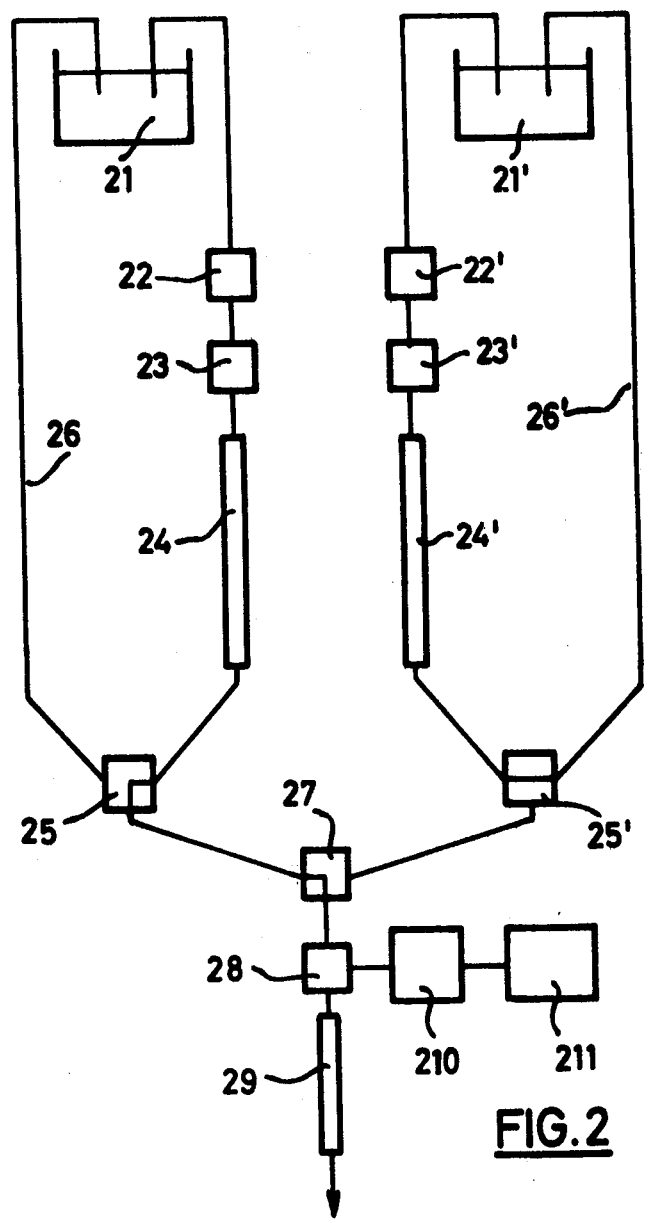
FIG. 2 is a schematic representation of an arrangement with two measuring channels.

In order to improve the utilization of the detector system, several streams of reagents can be connected in parallel to one detector cell, which is employed alternately for the various streams. A two-channel arrangement is shown in FIG. 2. 21 and 21' are stock vessels for two different reagents which are transported by pumps 22 and 22' through metering devices 23 and 23' into columns 24 and 24'. Using two three-way stopcocks 25 and 25', the streams can be fed either to the detector cell 28 or, through lines 26 and 26', back to the stock vessels 21 and 21'. In this way, even the channel which is not used is at all times ready to put into operation. 27 is a selector valve which serves to connect the channel actually in use to the detector cell 28 and the braking column 29. 210 and 211 are, respectively, the amplifier and recorder.

Figure 3:
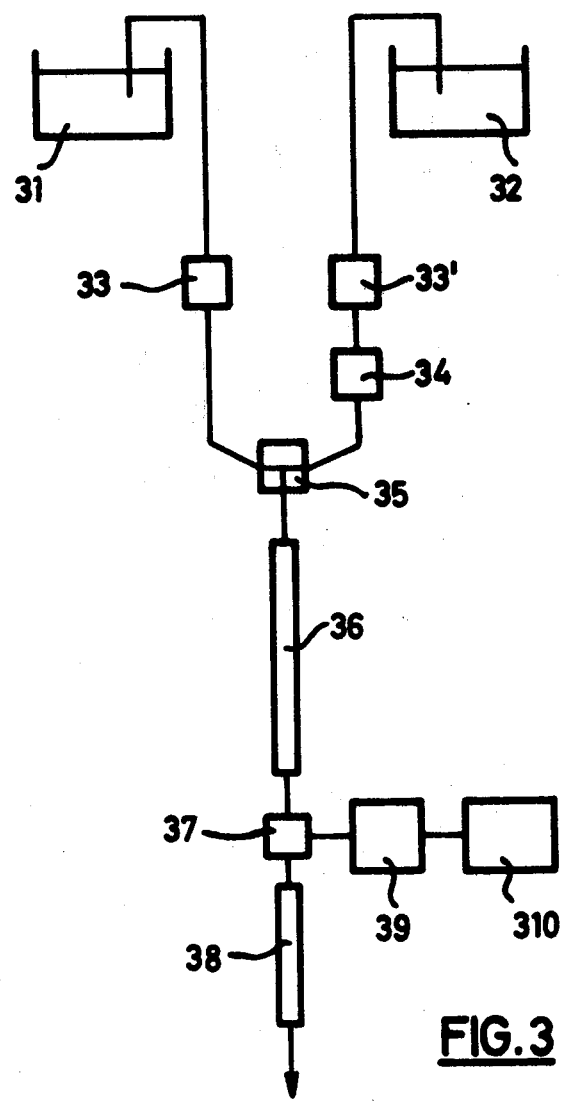
FIG. 3 is a schematic representation of a measuring device for setting up a defined volume ratio between sample and reagent.

FIG. 3 shows an example in which a precisely defined volume ratio of sample to reagent can be set up. 31 is a stock vessel for the reagent, and 32 the stock vessel for pure solvent, eg. water if aqueous solutions are being investigated. The mixing ratio is set by selecting the feed rate of pumps 33 and 33'. The sample is introduced into the stream of solvent through a metering device 34 in the form of a sample loop. In the T-piece 35, the two streams combine, and are then forced through a column 36, a detector cell 37 and a braking column 38. 39 and 310 are, respectively, the amplifier and recorder.

The same arrangement can be used if continuous production analysis is to be carried out. In that case, the pump 33' delivers sample instead of solvent. The metering device 34 may be used either periodically to introduce calibrating substance and hence check the correctness of the recorded values or, if the sample solution is a high and fluctuating blank reading, to introduce a part of the reagent, which is in that case not added to the reagent stock in the vessel 31. In this way the blank value of the sample can be eliminated, as described above.

I claim:

1. A process for analysis of aqueous or non-aqueous liquid solutions which comprises combining a sample of said liquid solutions with a stream of a liquid color reagent and reacting the sample and reagent under pressure as they pass through a chromatographic column which is filled with particles of inert, finely divided material with particle diameters in the range of 50 to 200 μm, and measuring the liquid reaction product in a photometric detector cell.

2. A process as set forth in claim 1, wherein the chromatographic column is heated.

3. A process as set forth in claim 1, wherein a stream of reagent and a stream of solvent are combined by means of pumps in order to achieve a defined ratio in which the reagent and sample are mixed, and the actual sample for analysis is introduced into the solvent stream by means of a sample loop.

4. A process as set forth in claim 1, wherein said finely divided material consists of glass beads of from 50 to 200 μm diameter.

* * * * *